(12) United States Patent
Green et al.

(10) Patent No.: US 11,776,118 B2
(45) Date of Patent: Oct. 3, 2023

(54) RECOGNITION OF PARTIALLY DIGESTED MEDICATIONS

(71) Applicant: INTERNATIONAL BUSINESS MACHINES CORPORATION, Armonk, NY (US)

(72) Inventors: William J. Green, Cary, NC (US); Brian W. Hart, Austin, TX (US); Anil Kalavakolanu, Austin, TX (US); Douglas Griffith, Round Rock, TX (US); Callum Foshee, Apex, NC (US)

(73) Assignee: International Business Machines Corporation, Armonk, NY (US)

( * ) Notice: Subject to any disclaimer, the term of this patent is extended or adjusted under 35 U.S.C. 154(b) by 475 days.

(21) Appl. No.: 17/109,188

(22) Filed: Dec. 2, 2020

(65) Prior Publication Data

US 2022/0172349 A1 Jun. 2, 2022

(51) Int. Cl.
*G06T 7/00* (2017.01)
*G16H 10/60* (2018.01)
(Continued)

(52) U.S. Cl.
CPC .......... *G06T 7/0012* (2013.01); *G06F 18/214* (2023.01); *G06N 5/04* (2013.01); *G06N 20/00* (2019.01); *G06V 20/00* (2022.01); *G16H 10/60* (2018.01); *G16H 15/00* (2018.01); *G16H 20/10* (2018.01); *G06T 2207/20081* (2013.01); *G06T 2207/30092* (2013.01)

(58) Field of Classification Search
CPC ......... G06T 7/0012; G06T 2207/20081; G06T 2207/30092; G16H 10/60; G16H 15/00; G16H 20/10; G06N 20/00; G06N 5/04; G06V 20/00; G06F 18/214
See application file for complete search history.

(56) References Cited

U.S. PATENT DOCUMENTS 6,535,637 B1   3/2003   Wootton et al.
6,574,580 B2   6/2003   Hamilton
(Continued)

FOREIGN PATENT DOCUMENTS

CN   101766575 A   7/2010
WO   2017064709 A1   4/2017

OTHER PUBLICATIONS

Fell et al., "Imaging and behaviour of solid oral dosage forms in vivo". (pp. 1-15) (Year: 1984).*
(Continued)

*Primary Examiner* — Manav Seth
(74) *Attorney, Agent, or Firm* — CANTOR COLBURN LLP; Tihon Poltavets

(57) ABSTRACT

Methods, systems and computer program products for recognition of partially digested medications are provided. Aspects include receiving an image depicting regurgitated stomach contents of an individual and obtaining medical data regarding the individual. Aspects also include analyzing the image, by a recognition model, to identify one or more pills depicted in the image and a percentage of the one or more pills that has not been digested. Aspects further include performing an action based on the medical data, the identification of the one or more pill and the percentage of the one or more pills that has not been digested.

20 Claims, 6 Drawing Sheets

(51) Int. Cl.
  *G16H 15/00* (2018.01)
  *G16H 20/10* (2018.01)
  *G06N 20/00* (2019.01)
  *G06N 5/04* (2023.01)
  *G06V 20/00* (2022.01)
  *G06F 18/214* (2023.01)

(56) References Cited

U.S. PATENT DOCUMENTS

| | | | | |
|---|---|---|---|---|
| 8,005,279 | B2* | 8/2011 | Yagi | A61B 1/042 |
| | | | | 382/128 |
| 8,448,846 | B2* | 5/2013 | Needhan | G06K 17/0022 |
| | | | | 235/487 |
| 8,771,176 | B2* | 7/2014 | Hendriks | A61B 18/20 |
| | | | | 600/173 |
| 9,060,950 | B2 | 1/2015 | Rosenberg | |
| 9,031,853 | B2* | 5/2015 | Bartfeld | G06Q 40/08 |
| | | | | 705/2 |
| 9,387,344 | B2* | 7/2016 | Sgouros | A61B 6/5217 |
| 9,511,078 | B2 | 12/2016 | Desai et al. | |
| 9,847,012 | B2* | 12/2017 | Zomet | G08B 21/24 |
| 10,980,404 | B2* | 4/2021 | Dray | A61B 1/041 |
| 2007/0268280 | A1* | 11/2007 | Fujita | A61B 1/00045 |
| | | | | 345/204 |
| 2009/0009332 | A1* | 1/2009 | Nunez | A01K 11/007 |
| | | | | 340/572.1 |
| 2009/0144087 | A1* | 6/2009 | Kelsch | G16H 10/60 |
| | | | | 705/3 |
| 2011/0195147 | A1* | 8/2011 | Drudis Sole | A23P 10/30 |
| | | | | 426/103 |
| 2015/0228179 | A1 | 8/2015 | Covannon et al. | |
| 2017/0286633 | A1* | 10/2017 | Ashoori | G16H 40/67 |
| 2018/0293357 | A1 | 10/2018 | Codella et al. | |

OTHER PUBLICATIONS

Mojaverian et al., "Gastrointestinal Transit of a Solid Indigestible Capsule as Measured by Radiotelemetry and Dual Gamma Scintigraphy" (pp. 719-724) (Year: 1989).*

* cited by examiner

RECOGNITION OF PARTIALLY DIGESTED MEDICATIONS

BACKGROUND

The invention relates generally to image processing and, more specifically, to the recognition of partially digested medications in an image.

When a person regurgitates after swallowing medications, it would beneficial to determine how much medication was absorbed by that person. The amount of absorbed medication cannot be accurately determined by weighing a regurgitated pill since the pill might have absorbed moisture which would cause a weight change. Also, waiting for the pill to dry might take hours or the pill might disintegrate.

SUMMARY

According to an embodiment, a system for recognition of partially digested medications is provided. The system includes a memory having computer readable computer instructions, and a processor for executing the computer readable instructions. The computer readable instructions include instructions for receiving an image depicting regurgitated stomach contents of an individual and obtaining medical data regarding the individual. The computer readable instructions also include instructions for analyzing the image, by a recognition model, to identify one or more pills depicted in the image and a percentage of the one or more pills that has not been digested. The computer readable instructions further include instructions for performing an action based on the medical data, the identification of the one or more pill and the percentage of the one or more pills that has not been digested.

According to another embodiment, a method for recognition of partially digested medications is provided. The method includes receiving an image depicting regurgitated stomach contents of an individual and obtaining medical data regarding the individual. The method also includes analyzing the image, by a recognition model, to identify one or more pills depicted in the image and a percentage of the one or more pills that has not been digested. The method further includes performing an action based on the medical data, the identification of the one or more pill and the percentage of the one or more pills that has not been digested.

According to a further embodiment, a computer program product is provided. The computer program product includes a computer readable storage medium having program instructions embodied therewith. The computer readable storage medium is not a transitory signal per se. The program instructions are executable by a computer processor to cause the computer processor to perform a method. The method includes receiving an image depicting regurgitated stomach contents of an individual and obtaining medical data regarding the individual. The method also includes analyzing the image, by a recognition model, to identify one or more pills depicted in the image and a percentage of the one or more pills that has not been digested. The method further includes performing an action based on the medical data, the identification of the one or more pill and the percentage of the one or more pills that has not been digested.

Additional features and advantages are realized through the techniques of the invention. Other embodiments and aspects of the invention are described in detail herein and are considered a part of the claimed invention. For a better understanding of the invention with the advantages and the features, refer to the description and to the drawings.

BRIEF DESCRIPTION OF THE DRAWINGS

The subject matter which is regarded as the invention is particularly pointed out and distinctly claimed in the claims at the conclusion of the specification. The foregoing and other features, and advantages of the invention are apparent from the following detailed description taken in conjunction with the accompanying drawings, in which:

DETAILED DESCRIPTION

Figure 1:
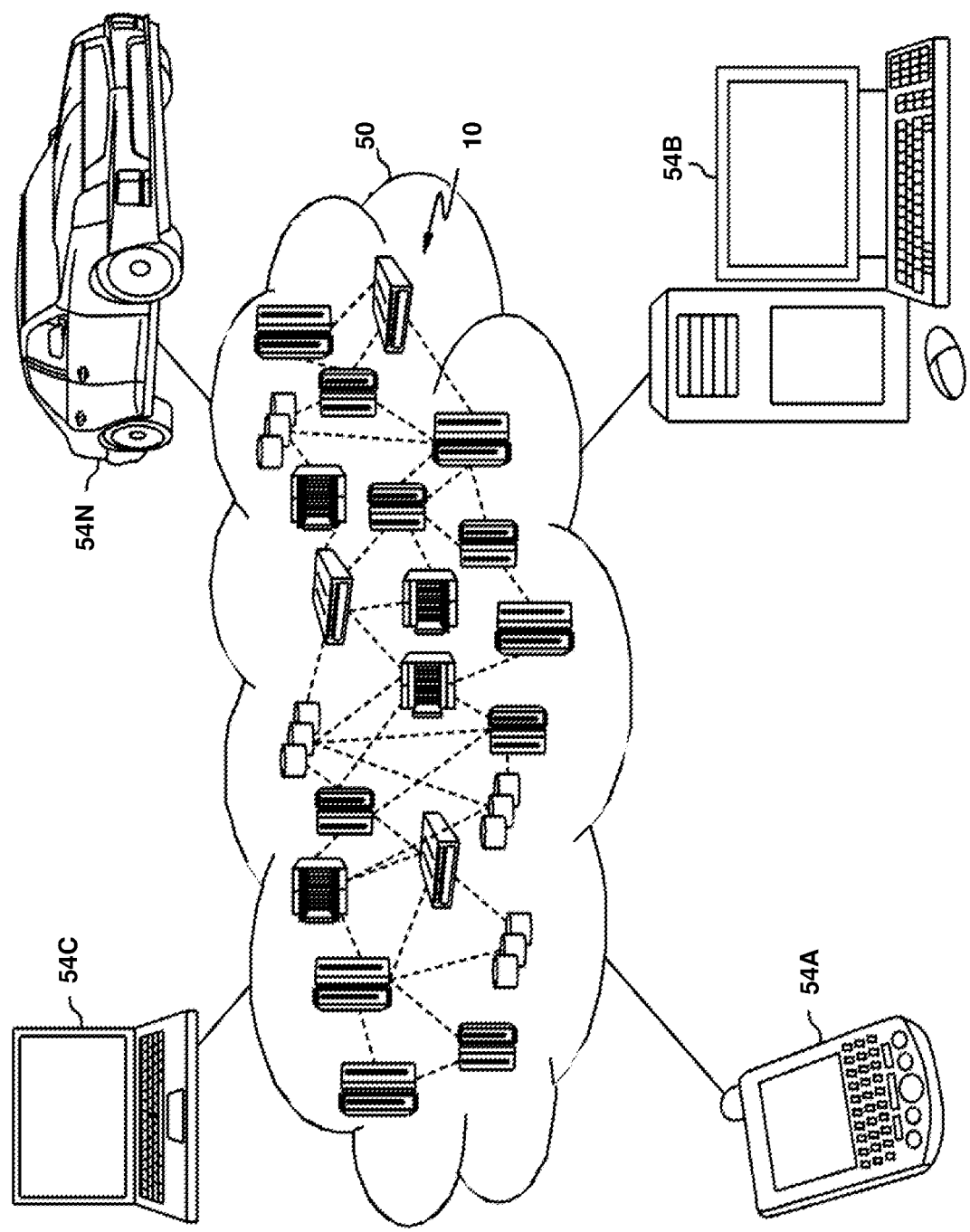
FIG. 1 depicts a cloud computing environment according to one or more embodiments of the present invention.

Various embodiments of the invention are described herein with reference to the related drawings. Alternative embodiments of the invention can be devised without departing from the scope of this invention. Various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" may be understood to include any integer number greater than or equal to one, i.e. one, two, three, four, etc. The terms "a plurality" may be understood to include any integer number greater than or equal to two, i.e. two, three, four, five, etc. The term "connection" may include both an indirect "connection" and a direct "connection."

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

For the sake of brevity, conventional techniques related to making and using aspects of the invention may or may not be described in detail herein. In particular, various aspects of computing systems and specific computer programs to implement the various technical features described herein are well known. Accordingly, in the interest of brevity, many conventional implementation details are only mentioned briefly herein or are omitted entirely without providing the well-known system and/or process details.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems; storage, deployed applications, and possibly limited control of select networking components (e.g., host firewalls).

Deployment Models are as follows:

Private cloud: the cloud infrastructure is operated solely for an organization. It may be managed by the organization or a third party and may exist, on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist, on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Referring now to FIG. 1, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 1 are intended to be illustrative only and that computing nodes 10 and cloud computing environment 50 can communicate with any type of computerized device over any type of network and/or network addressable connection (e.g., using a web browser).

Figure 2:
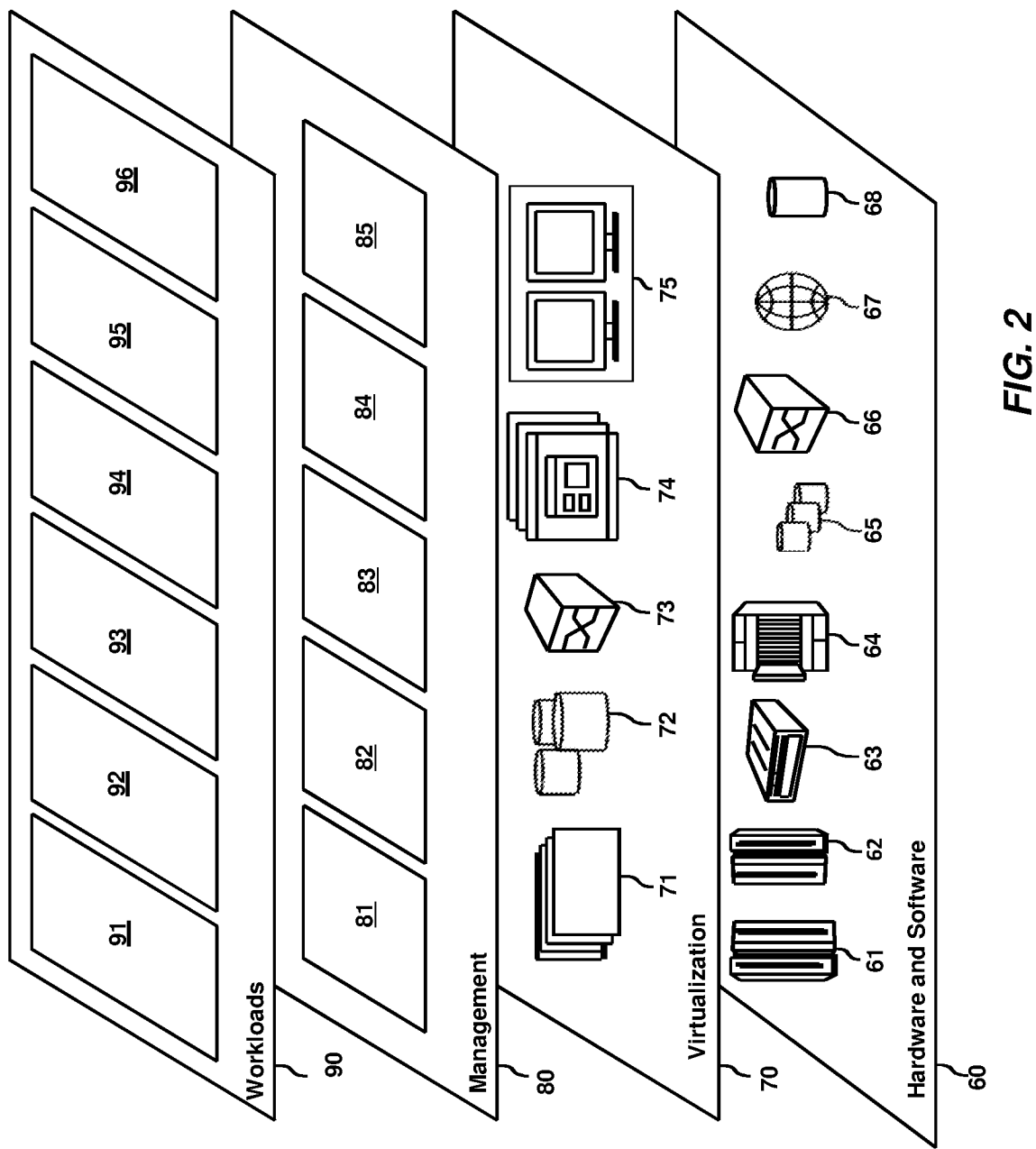
FIG. 2 depicts abstraction model layers according to one or more embodiments of the present invention.

Referring now to FIG. 2, a set of functional abstraction layers provided by cloud computing environment 50 (FIG. 1) is shown. It should be understood in advance that the components, layers, and functions shown in FIG. 2 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provides pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and recognition of partially digested medications 96.

Figure 3:
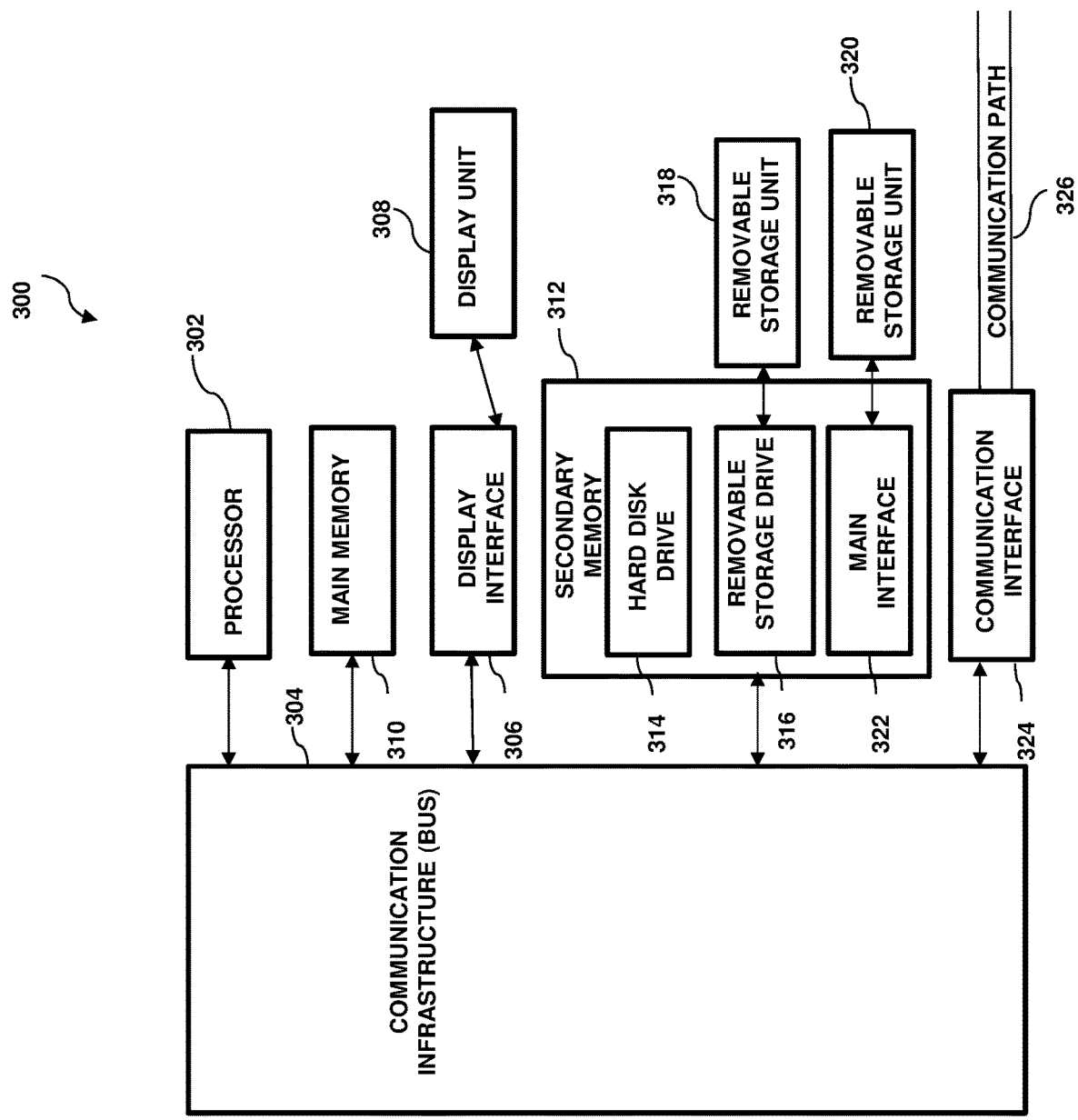
FIG. 3 depicts an exemplary computer system capable of implementing one or more embodiments of the present invention.

Turning now to a more detailed description of aspects of the present invention, FIG. 3 illustrates a high-level block diagram showing an example of a computer-based system 300 useful for implementing one or more embodiments of the invention. Although one exemplary computer system 300 is shown, computer system 300 includes a communication path 326, which connects computer system 300 to additional systems and may include one or more wide area networks (WANs) and/or local area networks (LANs) such as the internet, intranet(s), and/or wireless communication network(s). Computer system 300 and additional systems are in communication via communication path 326, (e.g., to communicate data between them).

Computer system 300 includes one or more processors, such as processor 302. Processor 302 is connected to a communication infrastructure 304 (e.g., a communications bus, cross-over bar, or network). Computer system 300 can include a display interface 306 that forwards graphics, text, and other data from communication infrastructure 304 (or from a frame buffer not shown) for display on a display unit 308. Computer system 300 also includes a main memory 310, preferably random access memory (RAM), and may also include a secondary memory 312. Secondary memory 312 may include, for example, a hard disk drive 314 and/or a removable storage drive 316, representing, for example, a floppy disk drive, a magnetic tape drive, or an optical disk drive. Removable storage drive 316 reads from and/or writes to a removable storage unit 318 in a manner well known to those having ordinary skill in the art. Removable storage unit 318 represents, for example, a floppy disk, a compact disc, a magnetic tape, or an optical disk, etc. which is read by and written to by a removable storage drive 316. As will be appreciated, removable storage unit 318 includes a computer readable medium having stored therein computer software and/or data.

In some alternative embodiments of the invention, secondary memory 312 may include other similar means for allowing computer programs or other instructions to be loaded into the computer system. Such means may include, for example, a removable storage unit 320 and an interface 322. Examples of such means may include a program package and package interface (such as that found in video game devices), a removable memory chip (such as an EPROM or PROM) and associated socket, and other removable storage units 320 and interfaces 322 which allow software and data to be transferred from the removable storage unit 320 to computer system 300.

Computer system 300 may also include a communications interface 324. Communications interface 324 allows software and data to be transferred between the computer system and external devices. Examples of communications interface 324 may include a modem, a network interface (such as an Ethernet card), a communications port, or a PCM-CIA slot and card, etc. Software and data transferred via communications interface 324 are in the form of signals which may be, for example, electronic, electromagnetic, optical, or other signals capable of being received by communications interface 324. These signals are provided to communications interface 324 via communication path (i.e., channel) 326. Communication path 326 carries signals and may be implemented using wire or cable, fiber optics, a phone line, a cellular phone link, an RF link, and/or other communications channels.

In the present disclosure, the terms "computer program medium," "computer usable medium," and "computer readable medium" are used to generally refer to media such as main memory 310 and secondary memory 312, removable storage drive 316, and a hard disk installed in hard disk drive 314. Computer programs (also called computer control logic) are stored in main memory 310, and/or secondary memory 312. Computer programs may also be received via communications interface 324. Such computer programs, when run, enable the computer system to perform the features of the present disclosure as discussed herein. In particular, the computer programs, when run, enable processor 302 to perform the features of the computer system. Accordingly, such computer programs represent controllers of the computer system.

In exemplary embodiments, methods, systems, and computer program products for the recognition of partially digested medications in an image are provided. In exemplary embodiments, a recognition model is configured to identify one or more pills in an image of regurgitated stomach contents of an individual. The recognition model is further configured to determine a percentage of each identified pill that remains undigested. Once the percentage of undigested medications has been determined, various actions can be taken based on the type of medication, the percentage of the pill that remains undigested, and the medical information of the individual. The actions can include but are not limited to, determining a next time for an individual to take a dose of the medication, notifying a medical provider of the individual of the event, determining a next dosage and time for an individual to the medication, and the like.

In exemplary embodiments, recognition models are created by manufacturers of medications and trained using a plurality of images for each type of medication. Each of the plurality of images used during training of the recognition model includes a pill of a medication type and a known percentage of the medication remaining. In some embodiments, trained recognition models and remedial plans could be required by regulatory authorities as part of the market approval process for each type of medication.

Figure 4:
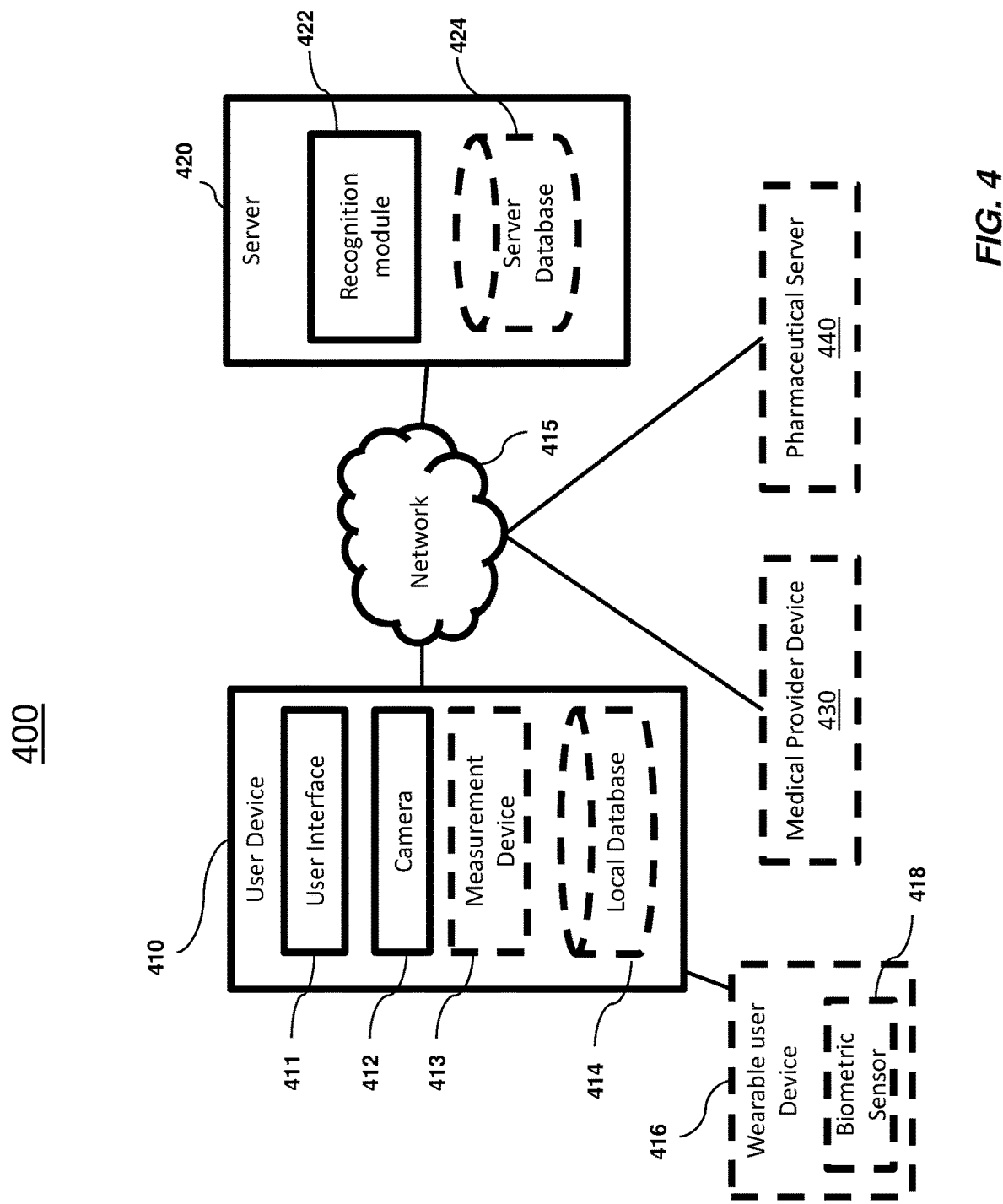
FIG. 4 depicts a system upon which recognition of partially digested medications may be implemented according to one or more embodiments of the present invention.

Turning now to FIG. 4, a system 400 upon which recognition of partially digested medications in an image may be implemented will now be described in accordance with an embodiment. The system 400 shown in FIG. 4 includes a server 420 in communication with a user device 410 via a communications network 415. The communications network 415 may be one or more of, or a combination of, public (e.g., Internet), private (e.g., local area network, wide area network, virtual private network), and may include wireless and wireline transmission systems (e.g., satellite, cellular network, terrestrial networks, etc.). In addition, the system 400 includes a medical provider device 430 and a pharmaceutical server 440. In exemplary embodiments, the user device 410 and the medical provider device 430 may be embodied in a computing system, such as the one shown in FIG. 3. In other embodiments, one or more of the user device 410 and the medical provider device 430 may be embodied in a smartphone, tablet, or any other suitable computing device. The server 420 and the pharmaceutical server 440 may be embodied in a computing system, such as the one shown in FIG. 3 or in a cloud computing system, such as the ones shown in FIGS. 1 and 2.

In exemplary embodiments, the user device 410 includes a user interface 411 and a camera 412. In one embodiment, the user interface 411 includes a touchscreen display that is configured to receive input from and provide information to a user. In one embodiment, the user device 410 includes a measurement device 413, such as a Lidar, Light Detection and Ranging, sensor that is configured to measure the size of items that are captured in images by the camera 412. Further, the user device 410 includes a local database 414 that is used to store medical data regarding one or more individuals, such as the user of the user device 410. The medical data can include, but is not limited to, a type of medication, and associated dosage information for an individual, medical providers associated with the individual, known medical conditions of an individual. In exemplary embodiments, the user device 410 is configured to store medical data for a plurality of individuals. In one example, the medical device 410 is configured to be used by a nurse and the medical data for each of the nurse's patients may be stored in the local database 414.

In exemplary embodiments, the user device 410 is configured to communicate with a wearable user device 416 that is disposed on an individual. The wearable user device 416 includes one or more biometric sensors 418 that are configured to measure one or more biometric characteristics of the user, such as blood pressure, blood oxygen level, heart rate, and the like. The wearable user device 416 is also configured to collect and store activity data of the user, such as step count, changes in heart rate, and the like.

In exemplary embodiments, the user device 410 is configured to transmit one or more images to a recognition module 422 on the server 420. In addition, the user device 410 can transmit medical data, including an indication of medications taken, or likely taken, by an individual during a time period prior to the images being captured. In exemplary embodiments, the recognition module 422 is configured to analyze the images received from the user device 410 and to identify one or more pills in the image along with a percentage of the pills that have not been digested. In exemplary embodiments, the recognition module 422 includes a plurality of trained recognition models that are stored in the server database 424. Each of the trained recognition models are trained using a plurality of images for each type of medication, where each of the plurality of images includes a pill of a medication type and a known percentage of the medication remaining. In one embodiment, the trained recognition models are obtained by server 420 from the pharmaceutical server 440.

In exemplary embodiments, the recognition module 422 selects which of the plurality of trained recognition models to utilize in analyzing the images based on the medical data obtained from the user device 410. In other embodiments, the recognition module 422 is configured to analyze the images using each trained recognition model. In exemplary embodiments, the recognition module 422 provides the user device 410 with the identification of each pill identified in the images provided, a percentage of the pills that have not been digested, and a confidence score for both the identification and the percentage.

In exemplary embodiments, the user device 410 is configured to transmit images captured by the camera and data obtained from the recognition model 422 to the medical provider device 430. In addition, the user device 410 is configured to transmit the identification of each pill identified in the images provided, a percentage of the pills that have not been digested, and a confidence score for both the identification and the percentage to the medical provider device 430. In one embodiment, the medical provider device 430 is a smartphone or tablet of a medical provider of the individual. The medical provider can use the medical provider device 430 to review the data received from the user device 410 and to communicate with the individual regarding what actions to take based on the data.

In one embodiment, the medical provider device 430 device provides a suggested course of action to the medical provider. The suggested course of action is obtained from the recognition module 422 based on the identification of each pill identified in the images provided, a percentage of the pills that have not been digested, and a confidence score for both the identification and the percentage. Upon reviewing the suggested course of action, the medical provider can agree with the suggested course of action or prescribe a different course of action for the individual to take. In exemplary embodiments, the actions taken by the medical provider via the medical provider device 430, i.e., accepting the suggested course of action or prescribing a different course of action, are provided to the user device 410 and the recognition module 422 of the server 420. In exemplary embodiments, the recognition module 422 is configured to adjust the suggested course of action based on the actions taken by the medical provider.

Figure 5:
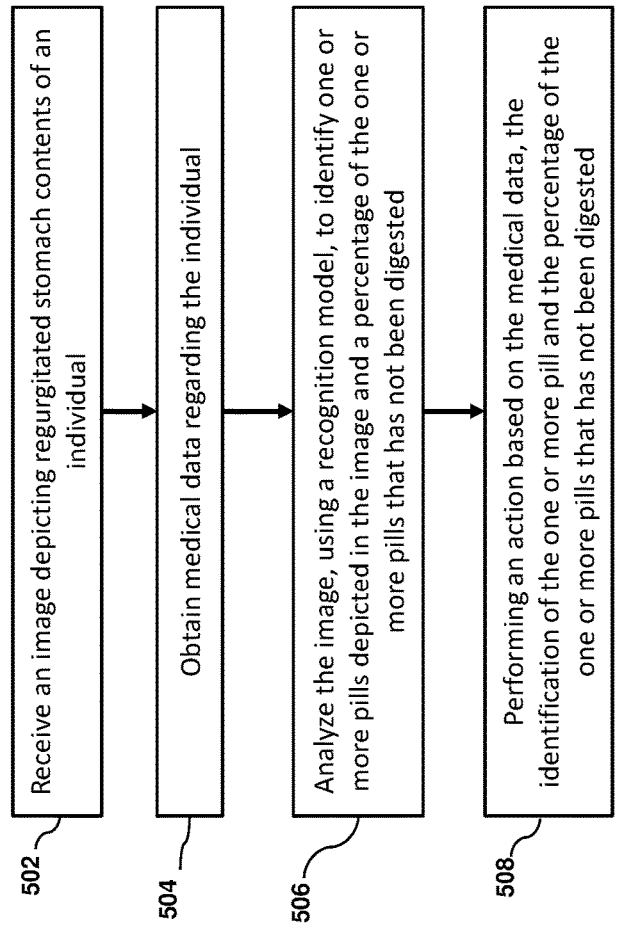
FIG. 5 depicts a flow diagram of a method for recognition of partially digested medications according to one or more embodiments of the present invention.

Turning now to FIG. 5, a flow diagram of a method 500 for recognition of partially digested medications in accordance with an embodiment is shown. The method 500 begins at block 502 and receives an image depicting the regurgitated stomach contents of an individual. Next, as shown at block 504, the method 500 includes obtaining medical data regarding the individual. In one embodiment, the medical data regarding the individual can be obtained from a user profile of the individual stored on the user device that captured the images. In another embodiment, the medical data regarding the individual can be obtained via the user interface of the user device. The medical data can include, but is not limited to, an indication of medications taken, or likely taken, by an individual during a time period prior to the images being captured.

Next, as shown at block 506, the method 500 includes analyzing the image, using a recognition model, to identify one or more pills depicted in the image and a percentage of the one or more pills that have not been digested. In exemplary embodiments, the recognition model is trained to identify the percentage of the one or more pills that have not been digested based at least in part on a plurality of training images that each include a partially dissolved pill and an indication of a remaining percentage of the partially dissolved pill. The recognition model is configured to provide an identification of the one or more pills depicted in the image, the percentage of the one or more pills that have not been digested, and confidence scores associated with the identification and the percentage. In exemplary embodiments, the recognition model is trained to identify the percentage of the one or more pills that have not been digested based at least in part on the identification of one or more medications that the individual has previously ingested.

As shown at block 508, the method 500 includes performing an action based on the medical data, the identification of the one or more pills, and the percentage of the one or more pills that have not been digested. In one embodiment, the action includes transmitting data including the image, the identification of the one or more pills, the percentage of the one or more pills that have not been digested, and the confidence scores to one or more recipients determined based at least in part on a user profile of the individual. The one or more recipients include a family member of the individual, a medical provider of the individual, and an emergency service provider. In exemplary embodiments, a determination of which of the one or more recipients to transmit the data to is based at least in part upon the medical data. In one example, the action may include contacting an emergency service provider based on determining that the individual has ingested and digested an amount of a specific type of medication that exceeds a threshold amount, i.e., that the individual has likely overdosed and is in need of medical attention. In another example, the action may include contacting a medical service provider of the individual based on determining that the individual has ingested and digested an amount of another type of medication that exceeds a prescribed amount of the medication.

In another embodiment, the action includes calculating a time for the individual to take a next pill of a type identified in the image based at least in part on the identification of the one or more pills depicted in the image, the percentage of the one or more pills that have not been digested, and the medical data. Likewise, the action may include calculating a next dosage amount of medication of a type identified in the image based at least in part on the identification of the one or more pills depicted in the image, the percentage of the one or more pills that have not been digested, and the medical data.

Figure 6:
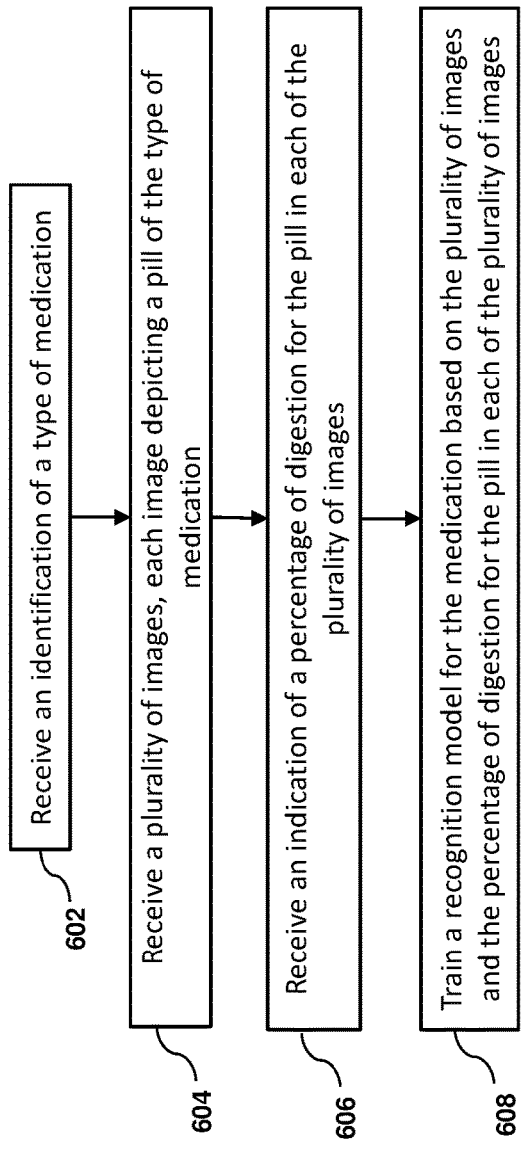
FIG. 6 depicts a flow diagram of a method for training a recognition model for identifying partially digested medications according to one or more embodiments of the present invention.

Turning now to FIG. 6, a flow diagram of a method 600 for training a recognition model for identifying partially digested medications in accordance with an embodiment is shown. The method 600 begins at block 602 by receiving an identification of a type of medication. Next, as shown at block 604, the method 600 includes receiving a plurality of images, each image depicting a pill of the type of medication. The method 600 also includes receiving an indication of a percentage of digestion for the pill in each of the plurality of images, as shown at block 606. The method 600 concludes at block 608 by training a recognition model for the medication based on the plurality of images and the percentage of digestion for the pill in each of the plurality of images. In exemplary embodiments, pharmaceutical manufacture creates the trained recognition model for a medication that they manufacture by allowing medication to partially dissolve in representative fluids for varying amounts of time and then photographing the partially dissolved pills. The partially dissolved pills are allowed to dry and the amount of remaining medication in each pill is measured and associated with the images. In exemplary embodiments, the photographs of the images include a reference, such as a measurement scale, or a pristine pill. In another embodiment, the photographs can be taken with a device that includes a Lidar sensor that is used to measure the size of the partially dissolved pills.

In exemplary embodiments, pharmaceutical manufacture makes the medications in a manner that that facilitates the use of visual models in determining a percentage of the pill that has been dissolved, for example by layering different colors within a pill. By manufacturing pills in a layered manner with different visual indications of the various layers, the accuracy of the trained recognition model can be increased. In exemplary embodiments, the pharmaceutical manufacture includes one or more recommended actions in the trained recognition model corresponding to each remaining medication amount. For example, the trained recognition model for a given medication may recommend an individual immediately take another dosage of the medication if the remaining percentage of the pill is above fifty percent. In exemplary embodiments, the trained recognition model also includes a physical description of a pill of the medication, such as dimensions and color, an indication of possible interactions and side effects of the medication, and adsorption rate information of the medication.

In exemplary embodiments, upon finding that a person has regurgitated a pill, a user device, such as a smartphone, is used to take a photograph of the partially dissolved pill. If the user device includes a measurement device, such as a Lidar sensor, the size of the partially dissolved pill is also captured. In cases where the user device does not include a measurement device, the user is prompted to ensure that a measurement reference standard is captured in the image. The measurement reference standard may be a pristine pill, a coin, a ruler, or any other item with a known size.

In exemplary embodiments, the user device includes an application that is configured to provide a friendly front-end to the recognition process, including prompting for steps and information such as, easy click to photograph, identification or selection of mediations recently taken (if known), and a reminder to include reference standard (if needed). In addition, the application is also configured to present remedial actions to the user, to provide links to reference information about the medications, and an option to contact a medical provider regarding the medication. In exemplary embodiments, contacting the medical provider includes transmitting the captured photograph of the partially dissolved pill and the results of the analysis of the recognition model to the medical provider.

In exemplary embodiments, the user device is configured to collect various medical data that can be used by the trained recognition and/or provided to a medical provider. The medical data can be directly inputted into the user device or it can be measure or inferred by the user device. The medical data can include a history of medications taken by an individual including a dosage of the medications, a time of ingestion, and a reason that the medication was taken, i.e., a sickness or malady of the individual. The medical data can also include an activity history of the individual that is obtained from a wearable device disposed on the individual, such as step count, heart rate history, and the like. The medical data may include an indication of an amount and type of liquids and food ingested with the medication and since the medication has been taken.

Technical benefits include an improved functionality of computer systems that are able to identify one or more partially digested pills in an image and to identify a percentage of the pills that have been digested. In one embodiment, identifying regurgitated pills and the percentage of the pills that have been digested, a correct dosage can be re-prescribed based on the absorbed amount, which can prevent overdoses as well as reducing the cost in cases where the medicine is very expensive. In another embodiment, an identification of regurgitated pills and the percentage of the pills that have been digested can be used by medical professionals to determine a treatment needed in the case of an overdose.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/ or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for recognition of partially digested medications comprising:
    receiving, by a processor, an image depicting regurgitated stomach contents of an individual;
    obtaining medical data regarding the individual;
    analyzing, by the processor, the image, by a recognition model, to identify one or more pills depicted in the image and a percentage of the one or more pills that has not been digested; and
    performing, by the processor, an action based on the medical data, the identification of the one or more pill and the percentage of the one or more pills that has not been digested.

2. The method of claim 1, wherein the recognition model is trained to identify the percentage of the one or more pills that has not been digested based at least in part on a plurality of training images that each include a partially dissolved pill and an indication of a remaining percentage of the partially dissolved pill.

3. The method of claim 1, wherein the medical data regarding the individual includes an identification of one or more medications that the individual has previously ingested.

4. The method of claim 3, wherein the recognition model is trained to identify the percentage of the one or more pills that has not been digested based at least in part on the identification of one or more medications that the individual has previously ingested.

5. The method of claim 1, wherein the recognition model is configured to provide an identification of the one or more pills depicted in the image, the percentage of the one or more pills that has not been digested, and confidence scores associated with the identification and the percentage.

6. The method of claim 5, wherein the action includes transmitting a data including the image, the identification of the one or more pills, the percentage of the one or more pills that has not been digested, and the confidence scores to one or more recipients determined based at least in part on a user profile of the individual.

7. The method of claim 6, wherein the one or more recipients include a family member of the individual, a medical provider of the individual, and an emergency service provider and wherein a determination of which of the one or more recipients to transmit the data to is based at least in part upon the data.

8. The method of claim 1, wherein the action includes calculating a time for the individual to take a next pill of a type identified in the image based at least in part on the identification of the one or more pills depicted in the image, the percentage of the one or more pills that has not been digested, and the medical data.

9. A system for recognition of partially digested medications, comprising:
    a memory having computer readable instructions; and
    a processor for executing the computer readable instructions, the computer readable instructions including instructions for:
        obtaining medical data regarding an individual;
        analyzing an image, by a recognition model, to identify one or more pills depicted in the image and a percentage of the one or more pills that has not been digested; and
        performing an action based on the medical data, the identification of the one or more pill and the percentage of the one or more pills that has not been digested.

10. The system of claim 9, wherein the recognition model is trained to identify the percentage of the one or more pills that has not been digested based at least in part on a plurality of training images that each include a partially dissolved pill and an indication of a remaining percentage of the partially dissolved pill.

11. The system of claim 9, wherein the medical data regarding the individual includes an identification of one or more medications that the individual has previously ingested.

12. The system of claim 11, wherein the recognition model is trained to identify the percentage of the one or more pills that has not been digested based at least in part on the identification of one or more medications that the individual has previously ingested.

13. The system of claim 9, wherein the recognition model is configured to provide an identification of the one or more pills depicted in the image, the percentage of the one or more pills that has not been digested, and confidence scores associated with the identification and the percentage.

14. The system of claim 13, wherein the action includes transmitting a data including the image, the identification of the one or more pills, the percentage of the one or more pills that has not been digested, and the confidence scores to one or more recipients determined based at least in part on a user profile of the individual.

15. The system of claim 14, wherein the one or more recipients include a family member of the individual, a medical provider of the individual, and an emergency service provider and wherein a determination of which of the one or more recipients to transmit the data to is based at least in part upon the data.

16. The system of claim 9, wherein the action includes calculating a time for the individual to take a next pill of a type identified in the image based at least in part on the identification of the one or more pills depicted in the image, the percentage of the one or more pills that has not been digested, and the medical data.

17. A computer program product comprising a computer readable storage medium having program instructions embodied therewith the program instructions executable by a computer processor to cause the computer processor to perform a method, comprising:

receiving an image depicting regurgitated stomach contents of an individual;

obtaining medical data regarding the individual;

analyzing the image, by a recognition model, to identify one or more pills depicted in the image and a percentage of the one or more pills that has not been digested; and performing an action based on the medical data, the identification of the one or more pill and the percentage of the one or more pills that has not been digested.

18. The computer program product of claim 17, wherein the recognition model is trained to identify the percentage of the one or more pills that has not been digested based at least in part on a plurality of training images that each include a partially dissolved pill and an indication of a remaining percentage of the partially dissolved pill.

19. The computer program product of claim 17, wherein the medical data regarding the individual includes an identification of one or more medications that the individual has previously ingested.

20. The computer program product of claim 19, wherein the recognition model is trained to identify the percentage of the one or more pills that has not been digested based at least in part on the identification of one or more medications that the individual has previously ingested.

* * * * *